(12) United States Patent
Nicq

(10) Patent No.: US 9,575,009 B2
(45) Date of Patent: Feb. 21, 2017

(54) REMOTE CONNECTION SYSTEM FOR AN AIRCRAFT

(71) Applicant: SNECMA, Paris (FR)

(72) Inventor: Geoffroy Nicq, Thomery (FR)

(73) Assignee: Snecma, Paris (FR)

( * ) Notice: Subject to any disclaimer, the term of this patent is extended or adjusted under 35 U.S.C. 154(b) by 0 days.

(21) Appl. No.: 14/900,388

(22) PCT Filed: Jun. 20, 2014

(86) PCT No.: PCT/FR2014/051543
§ 371 (c)(1),
(2) Date: Dec. 21, 2015

(87) PCT Pub. No.: WO2014/207353
PCT Pub. Date: Dec. 31, 2014

(65) Prior Publication Data
US 2016/0178531 A1     Jun. 23, 2016

(30) Foreign Application Priority Data

Jun. 27, 2013    (FR) ...................................... 13 56209

(51) Int. Cl.
*G01N 21/00*    (2006.01)
*G01N 21/88*    (2006.01)
(Continued)

(52) U.S. Cl.
CPC ........... *G01N 21/8806* (2013.01); *B64C 11/26* (2013.01); *F01D 21/003* (2013.01); *G01N 21/21* (2013.01);
(Continued)

(58) Field of Classification Search
CPC .......... B64D 47/02; F03D 11/00; B64C 27/54; B64C 2201/12; B64C 1/00
See application file for complete search history.

(56) References Cited

U.S. PATENT DOCUMENTS 3,723,722 A * 3/1973 Van Iderstine ......... B64C 27/00
                                                244/17.11
4,525,626 A    6/1985 Kush et al.
(Continued)

FOREIGN PATENT DOCUMENTS

EP    1 780 523 A1    5/2007

OTHER PUBLICATIONS

English Translation of Search Report mailed on Oct. 6, 2014, in corresponding International PCT Application No. PCT/FR2014/051543, filed on Jun. 20, 2014 (2 pages).

*Primary Examiner* — Tarifur Chowdhury
*Assistant Examiner* — Jamil Ahmed
(74) *Attorney, Agent, or Firm* — Bookoff McAndrews, PLLC

(57) ABSTRACT

The present description relates to a remote connection system suitable for being incorporated in an aircraft (1A, 1B, 1C) comprising at least one engine propeller (50A, 50B, 50C) having a plurality of blades (52A, 52B, 52C) suitable for rotating relative to a stationary module (10A, 10B, 10C) of the aircraft about an engine axis (X). The remote connection system comprises: a light emitter device configured, when the remote connection system is incorporated in the aircraft (1A, 1B, 1C), to emit a light beam that emerges to the outside of the propeller (50A, 50B, 50C), from at least one emission surface (54A, 54B, 54C) of said propeller (50A, 50B, 50C).

12 Claims, 4 Drawing Sheets

(51) Int. Cl.
    *B64C 11/26*     (2006.01)
    *F01D 21/00*     (2006.01)
    *G01N 21/21*     (2006.01)
    *B64D 45/00*     (2006.01)
    *B64D 27/00*     (2006.01)

(52) U.S. Cl.
    CPC . *B64D 2027/005* (2013.01); *B64D 2045/0085* (2013.01); *G01N 2021/8848* (2013.01); *G01N 2201/061* (2013.01); *G01N 2201/0683* (2013.01); *G01N 2201/08* (2013.01); *Y02T 50/66* (2013.01)

(56) References Cited

U.S. PATENT DOCUMENTS 8,348,611 B2 *   1/2013   Olesen .................. G01B 11/18
                                                          416/61
2013/0092786 A1 *   4/2013   Kellner .................. G01L 1/242
                                                          244/17.13

* cited by examiner

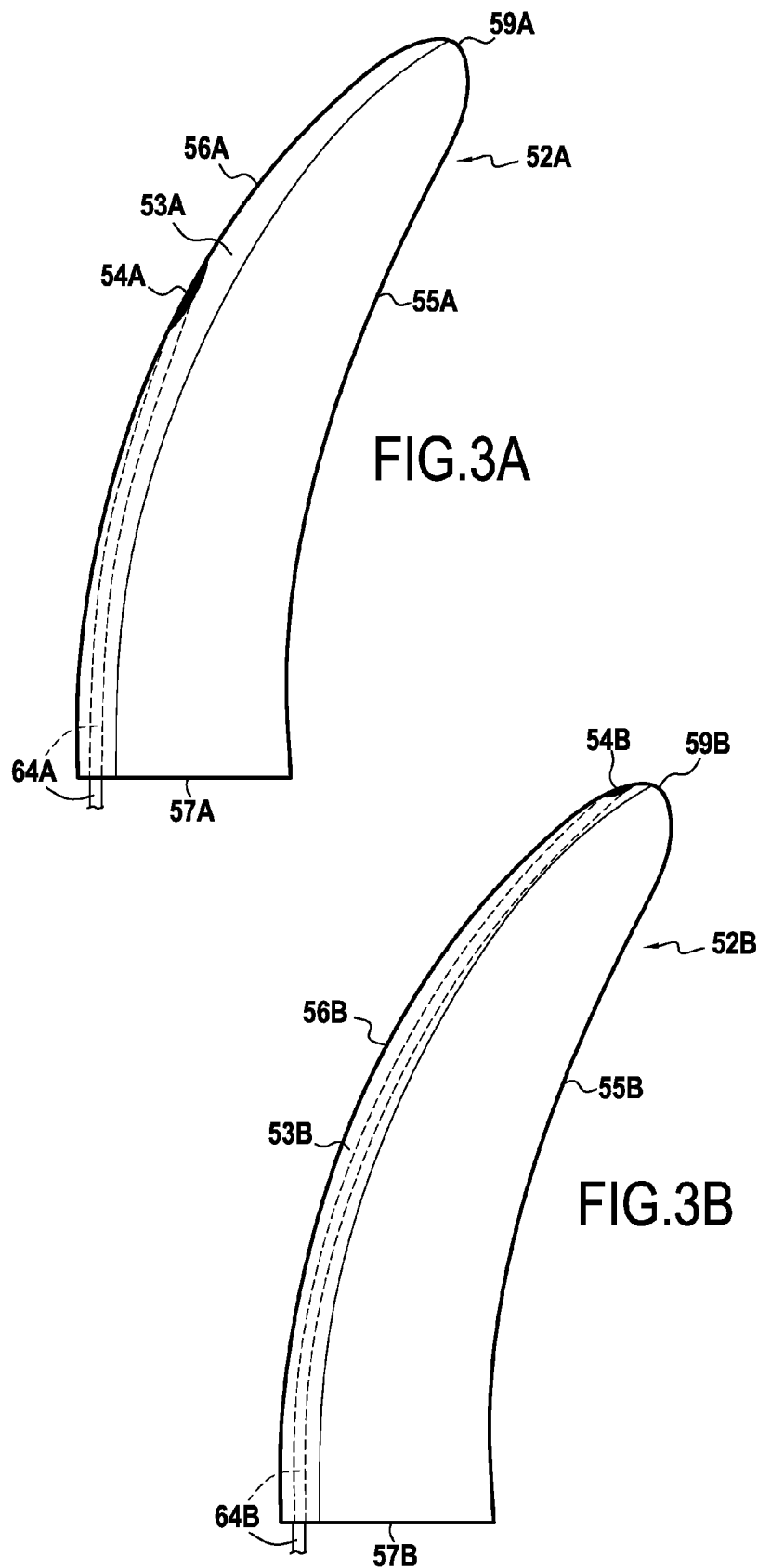

REMOTE CONNECTION SYSTEM FOR AN AIRCRAFT

CROSS-REFERENCE TO RELATED APPLICATIONS

This application is the U.S. national phase entry under 35 U.S.C. §371 of International PCT Application No. PCT/FR2014/051543, filed on Jun. 20, 2014, which claims priority to French Patent Application No. FR1356209, filed on Jun. 27, 2013, the entireties of each of which are incorporated by reference herein.

FIELD OF THE INVENTION

The present description relates to aircrafts, and it relates more particularly to the field of monitoring the health of blades of such engines, enclosed or not in a housing.

STATE OF THE PRIOR ART

The health of aircraft engine blades is often a critical factor that needs to be monitored, in particular when the blades are subjected to high levels of stress, as for example with the blades enclosed or not in a housing of turbine engines such as turboprops. Specifically, fatigue in a blade may lead to irreversible damage to the engine if it is not predicted soon enough.

A traditional technique for performing such monitoring consists in performing strength tests with deformation gauges.

Nevertheless, such deformation gauges are difficult to install and they are expensive, particularly since they generally present a lifetime that is short. Installing them on the blades of an engine in operation remains difficult because of the need to provide power and instrumentation on an engine that is rotating. Strain gauges are used for that purpose, but only to monitor blades that have been removed from an engine hub, which monitoring takes place under laboratory conditions, and thus does not enable a blade to be monitored while it is in operation, directly on the engine during flight cycles.

Furthermore, another well-known technique consists in determining the difference between firstly the time interval as measured between the instants at which predetermined respective locations on at least two successive blades actually pass in front of a stationary reference point, and secondly a theoretical time interval for the theoretical instants at which the same locations ought to pass, as calculated on the basis of the speed of rotation of the propeller; with variation in this difference being tracked over time. That technique makes it possible to determine indirectly both the degree of local deformation of a blade, at the predetermined location, relative to its original shape and/or the amplitude of the vibration to which that location is subjected. On that basis, it is possible to assess the degree of fatigue of the blade and to calculate its remaining lifetime.

It is known to apply that technique to a distal end of a blade (distal relative to the engine axis) as the predetermined location on the blade that is to be monitored. That technique is generally known as "tip timing".

Moreover, that technique is conventionally implemented by using capacitive or magnetic sensors, are arranged on a stationary portion of the aircraft and detecting the passage of the location of the blade that is monitored.

A drawback of that technique is that the capacitive or magnetic sensors used have a sensitivity that attenuates very quickly with increasing distance between the point at which the signal is emitted and the point at which the signal is detected. Consequently, that technique may be used only when the technology of the engine makes it possible for the spacing between the blade and the sensors mounted on the stationary portion of the aircraft to be small. For example, for engines of the open-rotor type or turboprops, it is very difficult to comply with that small spacing constraint and thus to ensure proper operation of the sensors.

There thus exists a need for monitoring that is less constraining to implement.

SUMMARY OF THE INVENTION

A first aspect of the present disclosure relates to a remote connection system suitable for being incorporated in an aircraft, said aircraft including at least one engine propeller having a plurality of blades suitable for rotating about an engine axis relative to a stationary module of the aircraft.

The remote connection system includes a light emitter device configured, when the remote connection system is incorporated in the aircraft, to emit a light beam that emerges to the outside of the propeller from at least one emission surface of said propeller; and a light detector device for detecting the light beam, including at least one detection surface that is sensitive to the light beam, and that is suitable for being incorporated in the stationary module so that said at least one emission surface and said at least one detection surface come repetitively to face each other remotely when the propeller is rotating relative to the stationary module.

A light beam may thus propagate between the at least one emission surface, which is intended to be fastened to the propeller, and said at least one detection surface, which is intended to be fastened to the stationary module. The at least one detection surface may thus be spaced apart from the propeller, and more particularly from said at least one emission surface. Consequently, the at least one detection surface may be stationary relative to the stationary module, while the propeller is rotating relative to the stationary module.

In addition, for a given spacing distance between said emission and detection surfaces, it has been found that it is much easier to obtain an attenuation of little significance for a light beam propagating between said surfaces, than with capacitive or magnetic signals.

Consequently, having recourse to an optical connection system implementing light emitter devices and light detector devices may enable blades to be monitored in a manner that is less constraining than performing monitoring in accordance with the above-mentioned prior art.

In particular, it is possible for the emission surface and detection surface to be spaced further apart from each other than with capacitive or magnetic systems, thereby making it less difficult to perform monitoring on engines of technology that does not allow small spacing distances between the emission and detection surfaces, as applies for example to engines of open-rotor type or turboprops.

In some embodiments, the remote connection system may be such that it comprises a plurality of detection surfaces spaced apart from one another.

Detection may thus be performed at a plurality of locations spaced apart from one another. The detection time resolution may thus be increased.

In some embodiments, the remote connection system may be such that, the blades of the propeller each presenting a leading edge and a trailing edge, said at least one emission surface is suitable for being incorporated in either one of the edges selected from the leading edge and the trailing edge of one of said blades of the propeller.

The leading edge and the trailing edge represent locations on the blade where mechanical stresses are large while the engine is in operation. It is therefore appropriate to seek to monitor the health of the blade in one of those locations.

In some embodiments, the remote connection system may be such that, the blades of the propeller each presenting a distal end relative to the engine axis, said at least one emission surface is suitable for being incorporated in the distal end of one of said blades of the propeller.

The distal end of a blade (i.e. the end of the blade that is the radially farthest away from the engine axis, as contrasted to its proximal end) represents the place where the blade is the most flexible, and thus where vibration is the greatest. A structural defect of the blade, giving rise to a variation in its stiffness, is thus more visible at the end of the blade than elsewhere.

In some embodiments, the remote connection system may be such that said at least one emission surface is suitable for being incorporated between the proximal and distal ends of the blade, radially remote from those two ends.

In some embodiments, the remote connection system may be such that the light emitter device comprises a light source suitable for being arranged remotely from the propeller; and at least one light guide suitable for being arranged inside a blade of the propeller so as to guide the light beam from the light source to said at least one emission surface.

It is thus possible to reduce significantly the cost of instrumenting a given blade of the propeller. Specifically, this blade may be monitored merely by incorporating a light guide in said blade, neither more nor less, the light source may be arranged remotely from this blade, in particular in the vicinity of the engine axis, and the light beam may be emitted from the emission surface of this blade after propagating along the light guide between the light source and this emission surface.

Furthermore, this configuration enables a light beam to be emitted from the propeller without any electrical contact being made on the propeller, since the light source is arranged remotely from said propeller. It is thus possible to overcome the technical difficulties that conventionally arise when setting up an electrical contact on a propeller, and in particular on its blades.

Moreover, thanks to this lack of electrical contact, replacing a blade that includes a light guide with another analogous blade is no more difficult than replacing a conventional blade with another blade, thereby simplifying maintenance of the propeller.

In some embodiments, the remote connection system may be such that the light emitter device includes a plurality of emission surfaces respectively suitable for being incorporated in a plurality of blades of the propeller, or in each blade of the propeller.

The light beam may thus be emitted to the outside of the propeller from a plurality of emission surfaces, each of these emission surfaces being intended to be fastened to a different blade. It is thus possible to monitor the health of a plurality of blades of the propeller, sequentially, in the order in which each of the emission surfaces passes successively in front of the detection surface.

In some embodiments, the remote connection system may be such that the light emitter device includes a plurality of light guides respectively suitable for being arranged inside the blades of the propeller intended to incorporate the emission surfaces.

Thus, a light beam may be emitted from a single light source, may then propagate through the various light guides, each of which is intended to be placed inside a different blade of the propeller, and finally emerging to the outside of the propeller from multiple locations corresponding to the various emission surfaces respectively suitable for being incorporated in the various blades that receive the light guides. Consequently, this configuration represents a solution that is simple and inexpensive for monitoring the health of a plurality of blades of the propeller.

In some embodiments, the remote connection system may be such that the light emitter device includes a shutter suitable for being arranged between the light source and the light guides in such a manner as to illuminate, among the light guides, only the or those that is/are situated within at least one predetermined angular range.

It is thus possible to illuminate only the or each of the few useful blades that, at any given time, is/are to be found inside at least one predetermined angular range, while the emission surface of the or one of these few useful blades is/are facing a detection surface.

The other blades, having their respective light guides lying outside said at least one predetermined angular range, are not illuminated by the light source, since the shutter constitutes an obstacle to such illumination. Under such circumstances, the propeller does not emit, from its outside circumference, too many point lights in succession which point lights, when observed from outside the aircraft, would otherwise together form illumination resembling the illumination from a garland of lights that might be troublesome and/or unattractive.

In some embodiments, the remote connection system may include an identification device for identifying the blades of the propeller.

Such an identification device may allow identifying individually, at will, at least one, or each, of the blades of the propeller moving past the detection surface, and thus establishing a correspondence between the various signals that are detected successively by the optical detection device and the various blades that pass successively in front of the detection surface.

In some embodiments, the remote connection system may be such that the identification device comprises a polarizing system configured to modify the phase or the color of the light beam for at least one of the emission surfaces.

In some embodiments, the polarizing system may comprise at least one polarizer intended to be secured in movement with the propeller and suitable for being arranged between the light source and the light guide of an emission surface.

In some embodiments, the remote connection system may be such that, the stationary module incorporating a structural element of a wing of the aircraft, said at least one detection surface is suitable for being incorporated in said structural element.

In some embodiments, the remote connection system may be such that, the stationary module incorporating a fuselage element of the aircraft, said at least one detection surface is suitable for being incorporated in said fuselage element.

In some embodiments, the remote connection system may be such that, the stationary module incorporating a nacelle for the propeller, said at least one detection surface is suitable for being incorporated in said nacelle. A second aspect of the present disclosure relates to a system suitable for being incorporated in an aircraft, the system including a stationary module, an engine propeller having a plurality of blades, and a remote connection system according to the above-described first aspect.

A third aspect of the present disclosure relates to an assembly for incorporating in an aircraft, the assembly comprising a system according to the above-described second aspect, and an engine having at least one rotor incorporating the propeller of the system and a stator incorporated in the stationary module of the system.

In some embodiments, the engine may be a turboprop. In some embodiments, the engine may be such that the blades of the propeller are not enclosed in a housing. The engine may then be of the so-called "open-rotor" type.

A fourth aspect of the present disclosure relates to an aircraft, incorporating at least one assembly of the third above-mentioned aspect.

The above-described characteristics and advantages, as well as others, will better appear on reading the following detailed description, of embodiments that have no limiting character and that are merely proposed by way of illustration. The detailed description refers to the accompanying drawings.

BRIEF DESCRIPTION OF THE DRAWINGS

The accompanying drawings are schematic and not to scale, and above all they seek to illustrate the principles mentioned in the present disclosure. In these accompanying drawings:

FIG. 3A is a profile view, in a radial plane, of a blade according to the first embodiment shown on its own, in which a light guide is incorporated;

FIGS. 1B, 2B, and 3B are figures analogous to FIGS. 1A, 2A, and 3A respectively, showing an aircraft having two assemblies, each provided with a remote connection system according to a second embodiment in accordance with the present disclosure.

DETAILED DESCRIPTION OF EMBODIMENTS

Figure 1A:
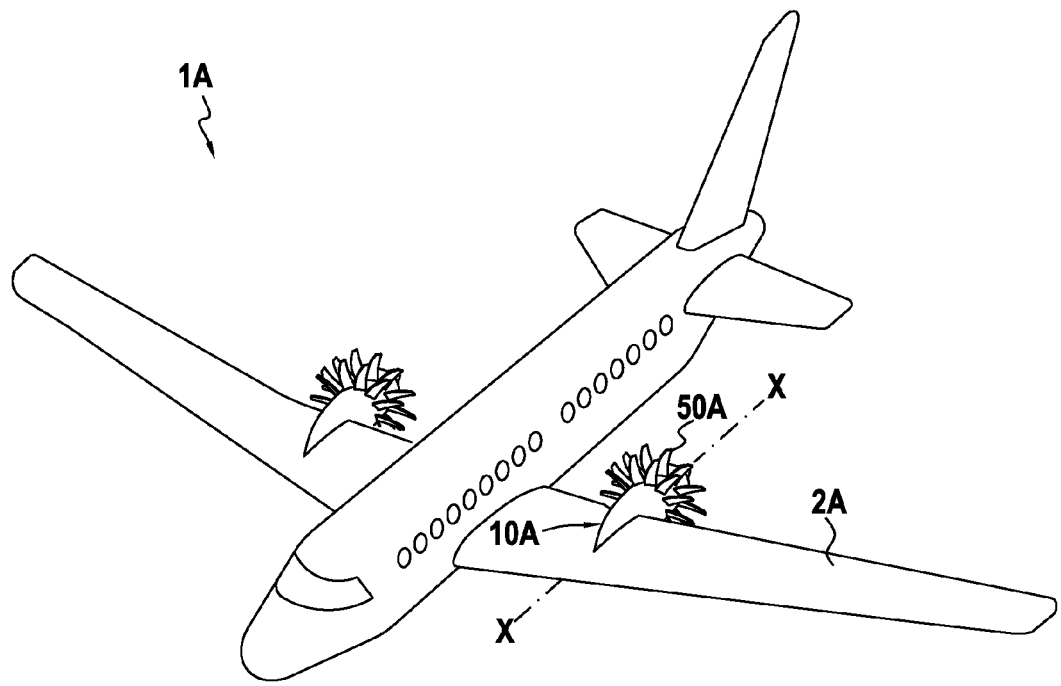
FIG. 1A is a schematic perspective view of an aircraft having two assemblies, each provided with a remote connection system according to a first embodiment in accordance with the present disclosure.
Figure 2A:
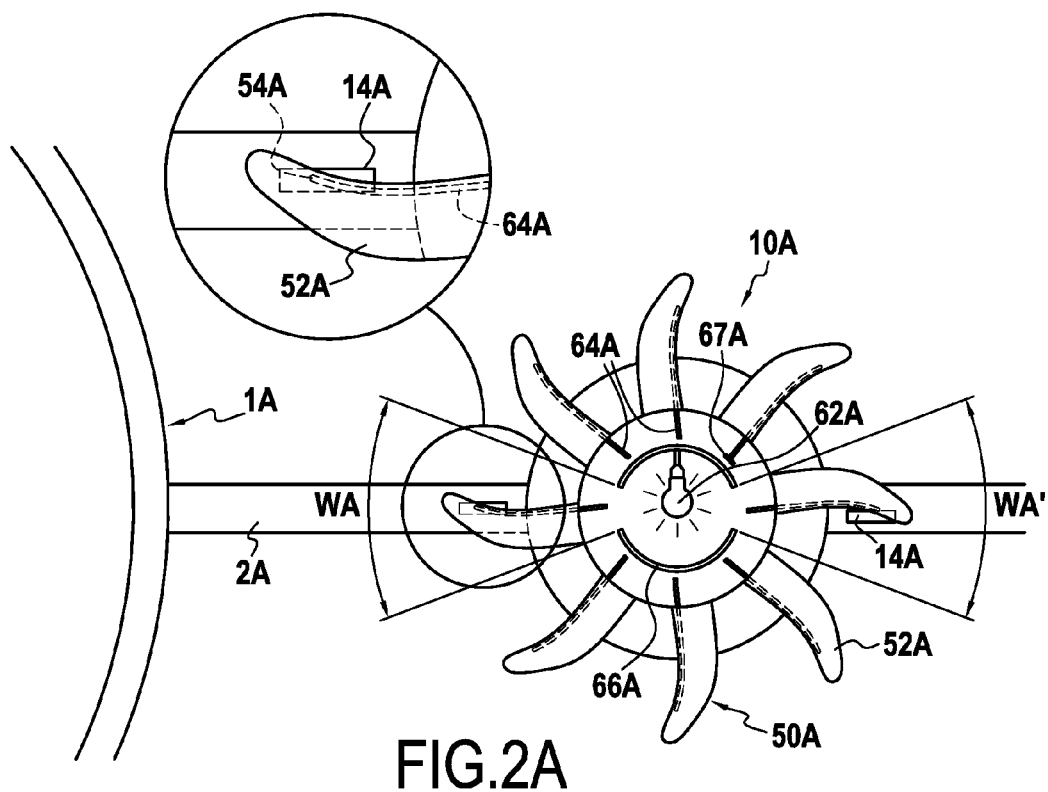
FIG. 2A is a fragmentary elevation view of the rear of the aircraft shown in FIG. 1A, with a detail view showing the emission surfaces of a blade going past the detection surfaces.

FIGS. 1A, 2A, and 3A are highly schematic views showing a first embodiment in accordance with the present disclosure of an aircraft 1A having two assemblies, each provided with a remote connection system.

Figure 1B:
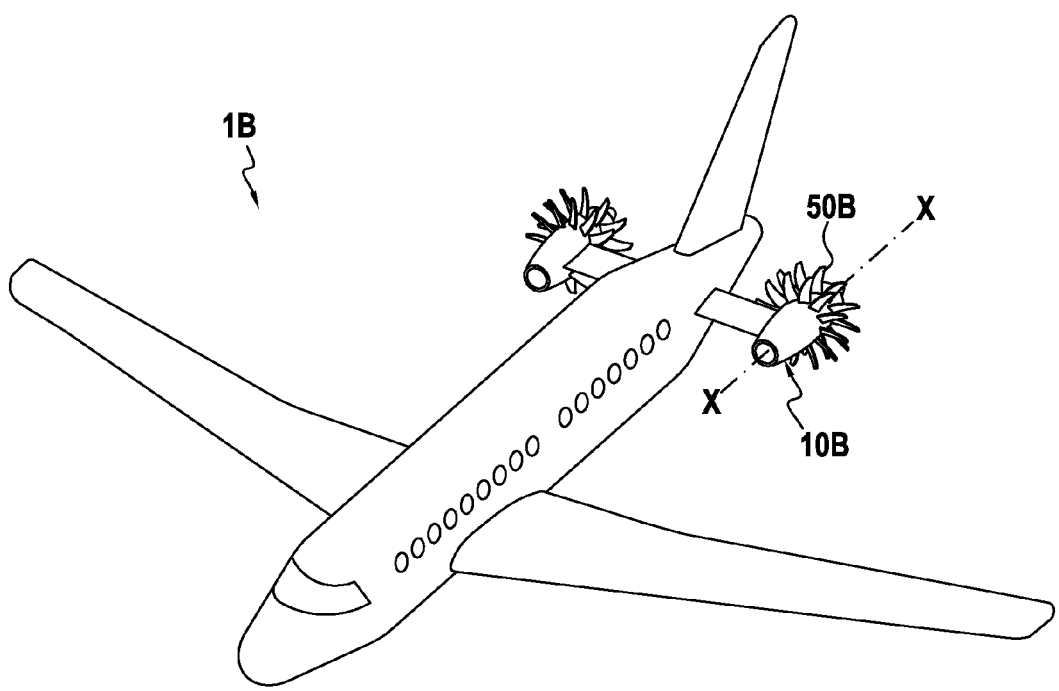
Figure 2B:
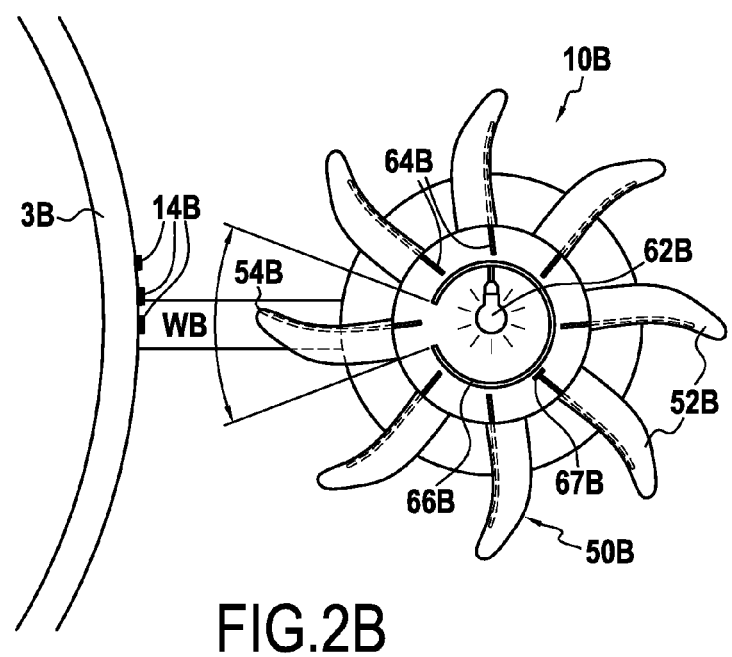

FIGS. 1B, 2B, and 3B are highly schematic views showing a second embodiment in accordance with the present disclosure of an aircraft 1B having two assemblies, each provided with a remote connection system.

Figure 4:
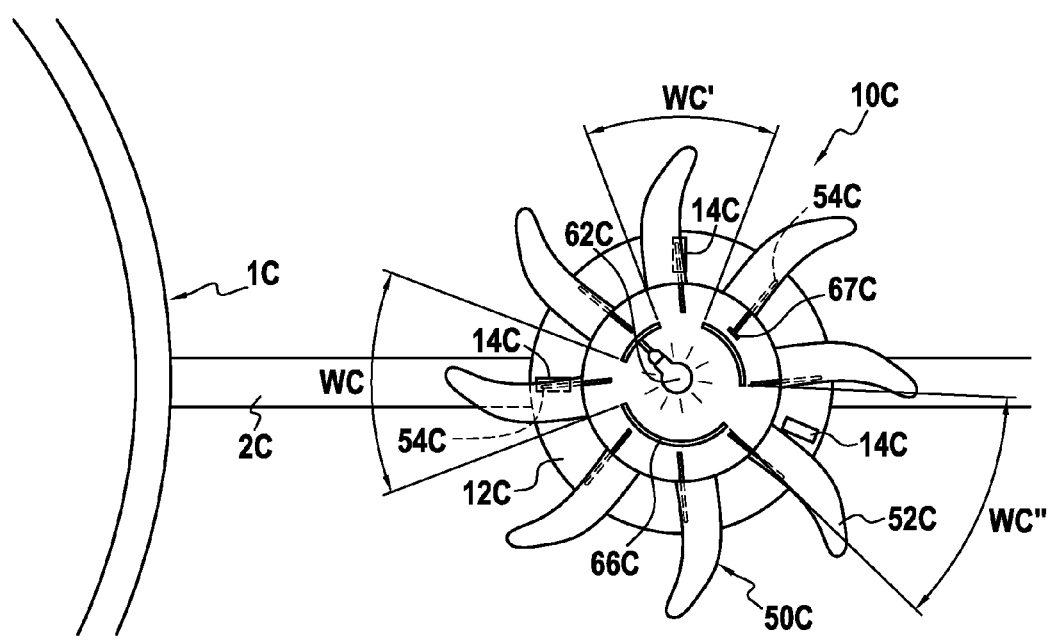
FIG. 4 is a view analogous to FIGS. 2A and 2B showing a third embodiment in accordance with the present disclosure.

FIG. 4 is a highly schematic view of a third embodiment in accordance with the present disclosure of an aircraft 1C having two assemblies, each provided with a remote connection system.

These first, second, and third embodiments present characteristics that are very analogous, so they are described simultaneously, for the sake of concision in the present disclosure. The numerical references relating to the first embodiment are given the suffix—A, whereas the numerical references given to the second embodiment are given that the suffix—B. Finally, the numerical references relating to the third embodiment are given the suffix—C.

In each of these three embodiments, the aircraft 1A, 1B, 1C includes two assemblies that are selected to be identical (form which it may be departed without departing from the scope of the present disclosure), such that only one of the two assemblies is described in detail, likewise for the sake of concision in the present disclosure.

In these embodiments, an assembly comprises: a stationary module 10A, 10B, 10C suitable for being incorporated in the aircraft 1A, 1B, 1C; an engine having both a stator incorporated in the stationary module and at least a rotor incorporating a propeller 50A, 50B, 50C having a plurality of blades 52A, 52B, 52C suitable for rotating relative to the stator about an engine axis X (shown in FIGS. 1A and 1B); and a remote connection system.

The propeller 50A, 50B, 50C, the stationary module 1A, 10B, 10C, and the remote connection system form a system in the meaning of the present disclosure.

In the first and second example, it is decided to provide the aircraft 1A, 1B with thruster type engines, each having two propellers 50A, 50B, each carrying a plurality of blades not enclosed in a housing. In these examples, these thruster engines are of the open-rotor type, and are themselves well-known. In these examples, both propellers are mounted at the rear of the engine, and they are also mounted to be contrarotating.

In the third example, it is decided to provide the aircraft 1C with engines having at least one tractor propeller (e.g. a single propeller), which engines are likewise themselves well-known.

Without departing from the scope of the present disclosure, it would also be possible to provide an engine having a single thruster propeller or an engine having two tractor propellers.

In these three examples, the remote connection system is an optical connection system. The remote connection system comprises a light emitter device configured, when the remote connection system is incorporated in the aircraft, to emit a light beam that emerges to the outside of at least one propeller 50A, 50B, 50C, from a plurality of emission surfaces 54A, 54B, 54C of said propeller 50A, 50B, 50C.

In the first and second examples, only one of the two propellers 50A, 50B, and in particular only the propeller that is farther upstream (relative to the travel direction of the air streams when the propellers are in their normal utilization conditions) incorporates such emission surfaces. Nevertheless, without departing from the scope of the present disclosure, provision could be made, if so desired, for engines in which both of the propellers, or in which only the propeller that is farther downstream, incorporate(s) at least one emission surface.

In these examples, the connection system comprises a light detector device for detecting the light beam, which device comprises at least one detection surface 14A, 14B, 14C that is sensitive to the light beam, the device being suitable for being incorporated in the stationary module 10A, 10B, 10C in such a manner that each emission surface 54A, 54B, 54C and said at least one detection surface 14A, 14B, 14C come to face each other repetitively and remotely when the propeller 50A, 50B, 50 is rotating relative to the stationary module 10A, 10B, 10C (see FIGS. 2A, 2B, and 4).

In the first example, the stationary module 10A incorporates a structural element of a wing 2A of the aircraft 1A, and said at least one detection surface 14A is suitable for being attached to said structural element.

In particular, in this example, the structural element is arranged in such a manner that said at least one detection surface 14A is on a trailing edge of the wing 2A of the aircraft 1A when said structural element is incorporated in the wing 2A. Moreover, this structural element may be formed integrally with the wing 2A or it may be a part that is fitted on the wing 2A.

Furthermore, in this example, the connection system has two detection surfaces 14A, suitable for being arranged on either side of the engine on the wing 2A. Nevertheless, without departing from the scope of the present disclosure, provision could be made, if so desired, for only one such surface, or indeed for more than two.

In this first example, the respective sites of these two surfaces on the wing 2A are deliberately arranged to be non-symmetrical relative to a plane containing the engine axis X so as to enable systematic noise in the detected signals to be reduced. In particular, these surfaces are offset vertically relative to each other.

Also, in this first example, the light flux emerging from the propeller 50A via the emission surface 54A is parallel to the direction of the engine axis X about which the propeller 50A is rotating. Furthermore, the detection surface 14A is plane and perpendicular to the engine axis X in this example.

In the second example, the stationary module 10B incorporates a fuselage element 3B of the aircraft 1B, and said at least one detection surface 14B is suitable for being attached to said fuselage element 3B.

In this second example, the fuselage element 3B may be formed integrally with the fuselage of the aircraft 1B or it may be a part fitted to the fuselage.

In this second example, the connection system has three detection surfaces 14B, respectively suitable for being incorporated in the fuselage element 3B at mutually distinct angular positions relative to the engine axis X. Nevertheless, without departing from the scope of the present disclosure, provision could be made, if so desired, for only one such surface, for two of them, or indeed for more than three.

In this second example, the respective sites of these three detection surfaces 14B on the fuselage element 3B are deliberately arranged to be non-symmetrical relative to a plane containing the engine axis X so as to enable systematic noise in the detected signals to be reduced. In particular, these surfaces are mutually angularly offset with angles that are not symmetrical.

Moreover, in this second example, the light flux emerging from the propeller 50B via the emission surface 54B propagates in a radial direction relative to the engine axis X, perpendicularly thereto.

In the third example, the stationary module 10C incorporates a nacelle 12C for the propeller 50C, and said at least one detection surface 14C is suitable for being attached to said nacelle 12C. This nacelle 12C may be a stationary portion of the engine, in well-known manner.

Furthermore, in this third example, the connection system comprises three detection surfaces 14C suitable for being arranged mutually angularly spaced apart on the nacelle 12C. Nevertheless, without departing from the scope of the present disclosure, provision could be made, if so desired, for only one such surface, for two of them, or indeed for more than three.

In this third example, the respective locations of these three detection surfaces 14C on the nacelle 12C are deliberately arranged to be non-symmetrical relative to a plane containing the engine axis X so as to enable systematic noise in the detected signals to be reduced. In particular, the surfaces are mutually spaced apart angularly in irregular manner.

Moreover, in this third example, the light flux emerging from the propeller 50C via the emission surface 54C is parallel to the direction of the engine axis X about which the propeller 50C is rotating. Furthermore, the detection surface 14C is plane and tilted relative to the engine axis X in this example.

Furthermore, in all three examples, the blades 52A, 52B, 52C of the propeller 50A, 50B, 50C each presents a respective leading-edge 56A, 56B, and a respective trailing edge 55A, 55B.

In the first and second examples, each of the emission surfaces 54A, 54B is incorporated in the leading edge 56A, 56B of the blade 52A, 52B of the propeller 50A, 50B in which the surface is respectively to be formed.

In the third example, each of the emission surfaces 54C is incorporated in the trailing edge of a blade of the propeller 50C in which the surface is respectively to be formed.

In the first example (see in particular FIG. 3A), each of the blades 52A of the propeller presents, in a radial direction relative to the engine axis X, a distal end 59A and a proximal end 57A relative to said engine axis X, and each of the emission surfaces 54A is formed remotely (in particular about halfway) in said radial direction from the proximal and distal ends 57A and 59A of the various blades 52A in which they are respectively incorporated.

The blades 52C of the third example are analogous to those of the first example, except that the emission surfaces 54C are formed closer in the radial direction to the proximal end than in the first example.

In the second example (see in particular FIG. 3B), each of the blades 52B of the propeller presents a distal end 59A and a proximal end 57B relative to the engine axis X, and the emission surfaces 54B are formed in the distal ends 57B and blades 52B in which they are respectively incorporated.

Furthermore, in all three examples, the light emission device comprises a light source 62A, 62B, 62C suitable for being arranged remotely from the propeller 50A, 50B, 50C; together with a plurality of light guides 64A, 64B, 64C respectively suitable for being arranged inside the blades 52A, 52B, 52C of the propeller 50A, 50B, 50C incorporating the emission surfaces 54A, 54B, 54C.

In particular, in the first and second examples, as shown in FIGS. 3A and 3B, the light guides 64A, 64B are housed inside reinforcements 53A, 53B of the leading edges 56A, 56B. This arrangement makes it possible to avoid affecting the composite structure of the blade 52A, 52B, and to avoid compromising its structural strength. Moreover, the light guides may be incorporated in the blades during a fabrication method step that is additional compared with the conventional method of fabricating blades, and that has no significant impact on the cost and the time required for fabricating the blades. Similarly, in the third example, the light guides 64C are housed inside a reinforcement of the trailing edge of the blades 52C.

In all three examples, a light guide 64A, 64B, 64C has a first end emerging from the proximal end of the blade 52A, 52B, 52C so as to come into the proximity of the light source 62A, 62B, 62C; and a second end of that opens into the leading edge 56A, 56B (trailing edge respectively) at a location embodying the emission surface 54A, 54B, 54C from which the light flux emerges from the blade 52A, 52B, 52C, to the outside of the blade.

Thus, the light guide 64A, 64B, 64C is suitable for guiding the light beam from the light source 62A, 62B, 62C to the emission surface 54A, 54B, 54C to enable the light beam to emerge from the blade 52A, 52B, 52C via said emission surface 54A, 54B, 54C.

In all three examples, the light source 62A, 62B, 62C is housed at least in part inside a hollow central portion present in the propeller 50A, 50B, 50C. In particular, the light source is spaced apart from the edges defining the hollow in said central portion so as to avoid rubbing against those edges when the propeller is rotating relative to the light source, which itself remains stationary. In particular, the light source 62A, 62B, 62C is secured to the stationary module. It is placed in the vicinity of the engine axis X, when observed in a plane perpendicular to said engine axis X.

Furthermore, in all three examples (see in particular FIGS. 2A, 2B, and 4), the light emitter device includes a shutter 66A, 66B, 66C suitable for being arranged between the light source 62A, 62B, 62C and the light guides 64A, 64B, 64C in such a manner as to illuminate, among the light guides 64A, 64B, 64C, only the or those that is/are situated within a predetermined angular range WA, WA' WB, WC, WC', WC".

In particular, in these examples, the shutter 66A, 66B, 66C is housed at least in part in the hollow central portion of the propeller 50A, 50B, 50C.

Morevoer, in these examples, the shutter 66A, 66B, 66C is in the overall form of a hollow cylinder. It is incorporated in the stationary module so that its own axis coincides with the engine axis X, and so that the light source 62A, 62B, 62C is housed at least in part in the hollow portion of the shutter 66A, 66B, 66C. The shutter also presents at least one empty angular fraction, through which the light emitted by the light source 62A, 62B, 62C may pass, and having edges that define said above-mentioned at least one angular range WA, WA', WB, WC, WC', WC".

In the first and third examples, the shutter 66A, 66C presents as many predetermined angular ranges WA, WA', WC, WC', WC" (and corresponding empty angular fractions) as the connection system has detection surfaces 14A, 14C, from which it may be departed without departing from the scope of the present disclosure, as shown in the second example, which has only one predetermined angular range WB (and only one corresponding empty angular fraction).

Furthermore, in all three examples, the remote connection system has a device for identifying the blades 52A, 52B, 52C of the propeller 50A, 50B, 50C.

In particular, in these examples, the identification device comprises a polarizing system that is configured to modify the phase or the color of the light beam for at least one emission surface 54A, 54B (in particular only one in each of the three examples, from which it may be departed without departing from the scope of the present disclosure).

In all three examples, the polarizing system comprises a polarizer 67A, 67B, 67C intended to be secured in movement to move with the propeller 50A, 50B, 50C and suitable for being arranged between the light source 62A, 62B, 62C and the light guide 64A, 64B, 64C of an emission surface 54A, 54B, 54C. In particular, the polarizer is secured to a hub of the propeller to which the blades are fastened.

The detection surface 14A, 14B, 14C is adapted to detect the difference in intensity or color that is induced by the polarizer 67A, 67B, 67C, thereby making it possible to distinguish the blade that is secured to the polarizer from the other blades.

Furthermore, without departing from the scope of the present disclosure, it is possible to couple the remote connection system to a system for processing the signal detected on said at least one detection surface of the detection device. To do this, it is possible to use a processor system analogous to that which is conventionally used for the conventional tip timing technique with a magnetic or capacitive sensor.

The embodiments or examples described in the present disclosure are given by way of nonlimiting illustration, and in the light of this disclosure, the person skilled in the art may easily modify these embodiments or examples or may envisage others, while remaining within the scope of the invention.

Furthermore, the various characteristics of these embodiments or examples may be used alone or in combination with one another. When they are combined, these characteristics may be combined as described above or in other ways, the invention not being limited to the specific combinations described in the present disclosure. In particular, unless specified to the contrary, a characteristic described with reference to one particular embodiment or example may be applied in analogous manner to another embodiment or example.

The invention claimed is:

1. A system suitable for being incorporated in an aircraft, the system comprising: a stationary module; an engine propeller having a plurality of blades suitable for rotating relative to the stationary module about an engine axis; and a remote connection system;
   wherein the remote connection system comprises:
      a light emitter device configured to emit a light beam that emerges to the outside of the propeller from at least one emission surface of said propeller; and
      a light detector device for detecting the light beam, the optical device including at least one detection surface that is sensitive to the light beam, and that is incorporated in the stationary module so that said at least one emission surface and said at least one detection surface come repetitively to face each other remotely when the propeller is rotating relative to the stationary module; and
   in that the light emitter device comprises a light source arranged remotely from the propeller; and at least one light guide arranged inside a blade of the propeller so as to guide the light beam from the light source to said at least one emission surface.

2. A system according to claim 1, wherein the remote connection system comprises a plurality of detection surfaces that are spaced apart from one another.

3. A system according to claim 1, wherein each of the blades of the propeller presents a leading edge and a trailing edge, and said at least one emission surface is incorporated in either one of the edges selected from the leading edge and the trailing edge of one of said blades of the propeller.

4. A system according to claim 1, wherein each of the blades of the propeller presents a distal end relative to the engine axis, and said at least one emission surface is incorporated in the distal end of one of said blades of the propeller.

5. A system according to claim 1, wherein the light emitter device comprises a plurality of emission surfaces incorporated in a respective plurality of blades of the propeller.

6. A system according to claim 5, wherein the light emitter device comprises a plurality of light guides arranged inside respective blades of the propeller that are to incorporate the emission surfaces.

7. A system according to claim 6, wherein the light emitter device includes a shutter arranged between the light source and the light guides in such a manner as to illuminate only the or each light guide that is situated within at least one predetermined angular range.

8. A system according to claim 5, wherein the remote connection system includes an identification device for identifying the blades of the propeller.

9. A system according to claim 8, wherein the identification device comprises a polarizing system configured to modify the phase or the color of the light beam for at least one of the emission surfaces.

10. A system according to claim 1, wherein the stationary module incorporates a structural element of a wing of the aircraft, and said at least one detection surface is incorporated in said structural element.

11. A system according to claim 1, wherein the stationary module incorporates a fuselage element of the aircraft, and said at least one detection surface is incorporated in said fuselage element.

12. A system according to claim 1, wherein the stationary module incorporates a nacelle for the propeller, and said at least one detection surface is incorporated in said nacelle.

* * * * *